United States Patent
Counter et al.

(10) Patent No.: US 8,927,598 B2
(45) Date of Patent: Jan. 6, 2015

(54) TREATING ONCOGENIC RAS DRIVEN CANCERS

(75) Inventors: Christopher M. Counter, Durham, NC (US); Kian-Huat Lim, Valley Park, MO (US); Brooke B. Ancrile, Annville, PA (US); David F. Kashatus, Carboro, NC (US)

(73) Assignee: Duke University, Durham, NC (US)

( * ) Notice: Subject to any disclaimer, the term of this patent is extended or adjusted under 35 U.S.C. 154(b) by 957 days.

(21) Appl. No.: 12/863,600

(22) PCT Filed: Jan. 9, 2009

(86) PCT No.: PCT/US2009/000170
§ 371 (c)(1),
(2), (4) Date: Aug. 5, 2010

(87) PCT Pub. No.: WO2009/099507
PCT Pub. Date: Aug. 13, 2009

(65) Prior Publication Data
US 2011/0003887 A1 Jan. 6, 2011

Related U.S. Application Data

(60) Provisional application No. 61/006,740, filed on Jan. 30, 2008.

(51) Int. Cl.
*A61K 31/35* (2006.01)
*C12N 15/113* (2010.01)
*A61K 31/198* (2006.01)

(52) U.S. Cl.
CPC .......... *C12N 15/1135* (2013.01); *A61K 31/198* (2013.01); *C12N 15/1137* (2013.01); *C12Y 114/13039* (2013.01); *C12N 2310/14* (2013.01)
USPC ......................................................... 514/453

(58) Field of Classification Search
USPC ......................................................... 514/453
See application file for complete search history.

(56) References Cited

U.S. PATENT DOCUMENTS

2005/0037455 A1 * 2/2005 Kolesnick et al. ........... 435/69.1
2007/0293453 A1    12/2007 Fisher et al.

OTHER PUBLICATIONS

Hofseth et al., Nitric Oxide in Cancer and Chemoprevention, Free Radical Biology & Medicine 2003, 34(8): 955-968, p. 958, Table 2; p. 959, col. 1; p. 960, col. 2; p. 961, col. 1; p. 961, Table 3.
Gupta et al., Morphine Stimulates Angiogenesis by Activitating Proangiogenic and Survival Promoting Signaling and Promotes Breast Tumor Growth, Cancer Research 2002, 62;4491-4498; p. 4491, Introduction; p. 4494, col. 1; p. 4496, col. 2.

* cited by examiner

*Primary Examiner* — Jon E Angell
(74) *Attorney, Agent, or Firm* — Bacon & Thomas, PLLC

(57) ABSTRACT

Oncogenic Ras-driven cancer is treated with agent by interrupting pathway comprising activation of Akt by oncogenic Ras, activated Akt causing phosphorylation of eNOS at S1177 site of eNOS to provide activated eNOS in cancer cells and activated eNOS causing activation of wildtype Ras by nitrosylation thereof at C118 to provide GTP-bound activated wildtype H and N Ras. L-NAME can be orally administered to interrupt this pathway. Wortmannin can be administered intravenously to interrupt this pathway. Novel siRNAs are disclosed useful to interrupt said pathway.

5 Claims, 1 Drawing Sheet

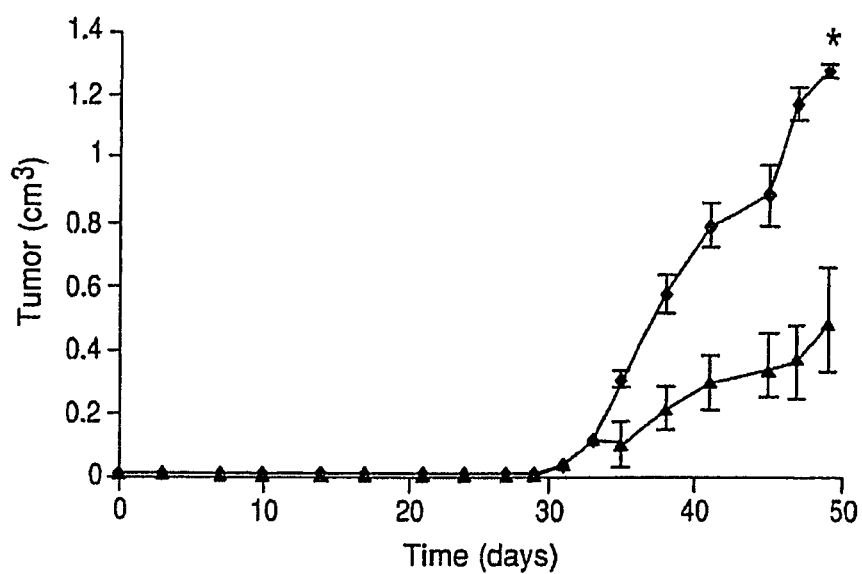

US 8,927,598 B2

TREATING ONCOGENIC RAS DRIVEN CANCERS

CROSS-REFERENCE TO RELATED APPLICATIONS

This application claims the benefit of U.S. Provisional Application No. 61/006,740, filed Jan. 30, 2008, the whole of which is incorporated herein by reference.

This invention was made at least in part with Government support under National Institutes of Health Grant Nos. R01CA094184 and R01 CA 118378. The Government has certain rights in the invention.

FIELD OF THE INVENTION

This invention is directed to method of treating oncogenic Ras driven cancers by inter alia interfering with eNOS and correspondingly the nitrosylation of wildtype Ras proteins.

BACKGROUND OF THE INVENTION

The small GTPase family of Ras proteins composed of N-, K- and H-Ras function as GDP/GTP-regulated binary switches that normally relay signals from extracellular stimulus-activated cell surface receptors to diverse cytoplasmic signaling networks in a regulated fashion. Ras is mutated to remain in a stimulus-independent, constitutively active GTP-bound state in one-third of tumors. (referred to herein as oncogenic Ras). Therefore oncogenic Ras has been a desirable target for cancer-therapy. However, oncogenic Ras has proven refractory to attempts to inhibit its activity in a clinical setting.

SUMMARY OF THE INVENTION

It has been discovered herein that the pathway for oncogenic Ras driven cancers comprises oncogenic Ras activating Akt (also known as protein kinase B), activated Akt causing phosphorylation at S1177 of eNOS and activation of eNOS in the cancer cells and activated eNOS in turn causing nitrosylation of wildtype HRas and NRas proteins at C118 in cancer cells and activation of the wild type Ras proteins, providing GTP-bound Ras in inchoate and mature cancer cells, and promoting tumorigenesis and tumor growth in these cells (pathway termed Akt-eNOS-(wildtype) Ras pathway), and it is further discovered herein that interrupting this pathway inhibits tumorigenesis and tumor growth and that blocking phosphorylation of eNOS, e.g. by knocking down expression of eNOS, inhibits tumor initiation and maintenance and that blocking the provision of nitrosylated wildtype HRas and NRas, but not oncogenic KRas inhibits tumor maintenance (growth).

Thus, one embodiment herein is directed to a method of treating an oncogenic Ras driven cancer in a patient comprising administering to said patient a therapeutically effective amount of an inhibitor of activation of Akt by oncogenic Ras or a therapeutically effective amount of inhibitor of activation by activated Akt of eNOS, or a therapeutically effective amount of inhibitor of expression of eNOS or therapeutically effective amount of inhibitor of eNOS catalytic activity, or a therapeutically effective amount of inhibitor of expression or activity of wildtype HRas or NRas or a therapeutically effective amount of an inhibitor of activation of wildtype Ras by activated eNOS-mediated nitrosylation.

Another embodiment herein is directed to novel siRNAs, in one case for knocking down the expression of eNOS, in another case for knocking down the expression of NRas protein. In the first case the novel siRNA has the sequence set forth in the Sequence Listing as SEQ ID No: 1. In the second case the novel siRNA has the sequence set in the Sequence Listing as SEQ ID No: 2.

BRIEF DESCRIPTION OF THE DRAWINGS

FIG. 1 is a graph of tumor volume versus time and shows results of Background Example 2.

DETAILED DESCRIPTION

We turn firstly to the oncogenic Ras driven cancers treated herein. These included pancreatic cancer, non-small-cell lung adenocarcinoma, colorectal cancer, follicular thyroid cancer, undifferentiated papillary thyroid cancer, seminoma, melanoma, bladder cancer, liver cancer, kidney cancer, myelodysplastic syndrome and acute myelogenous leukemia. The cancers treated herein exclude ovarian cancer.

We turn now to inhibitors of activation of Akt by oncogenic Ras.

One class of agents useful for this purpose is constituted of phosphoinoside 3'-hydroxykinase (P13K) inhibitors. This is because P13K is essential for oncogenic Ras activation of Akt.

A test for determining P13K inhibitors is the detection of phosphorylated Akt by immunoblot with a phospho-specific antibody.

Useful P13K inhibitors and dosages thereof for inhibiting activation of Akt and therefore of activated Akt activation of eNOS and dosages thereof are wortmannin (dosage 10 to 500 nM concentration in blood), 2-(4-morpholinyl)-8-phenyl-4H-1-benzopyran-4-one (LY294002) (dosage 0.5-5 μm concentration in blood), and quercetin (dosage 0.1-500 mg).

We turn to inhibitors of the activation by activated Akt of eNOS, i.e., which prevent phosphorylation at the S1177 site of eNOS.

These can be determined by testing for compounds which cause a loss of activated Akt caused phosphorylation at S1177 of eNOS by immunoblot by using commercially available phosphor-S1177 eNOS antibody.

Useful inhibitors of the activation by activated Akt of eNOS and dosage thereof for inhibiting activation by activated Akt of eNOS is GSK690693 (dosage 10-30 mg/kg based on animal studies).

We turn to inhibitors of expression of eNOS, i.e., which prevent or reduce expression of eNOS.

One agent useful for this purpose is a novel siRNA generated by the applicant identified in the Sequence Listing as SEQ ID NO: 1; that efficiently knocks down the expression of human eNOS and blocks tumor initiation and growth of cancer cell lines in mice and is considered to do the same in humans. The siRNA of SEQ ID NO:1 is produced as follows: Complementary oligonucletides obtained from Integrated DNA Technologies (Coralville, USA) and annealed together were cloned into the Hind III and Bgl II sites of pSUPER-RETRO (OligoEngine, Seattle, Wash.). The sense strand of this insert is identified in the Sequence Listing as SEQ ID NO: 4. Transcription of this sequence by RNA polymerase produces an shRNA having the Sequence Listing as SEQ ID NO: 5. This is processed using Dicer complex to remove the hairpin to give the double stranded RNA sequence of SEQ ID NO: 1 which specifically knocks down the expression of human eNOS Exemplary dosage is 100-1600 micrograms based on a clinical trial of the siRNA compound AGN211745.

A test for determining that eNOS expression is reduced is by immunoblot by using commercially available phosphor-S1177 eNOS antibody.

We turn to inhibitors of eNOS, i.e., which inhibit catalytic activity of eNOS.

Classes of agents useful for this purpose are both general and isoform-specific substrate analogs and dimerization analogs that inhibit catalytic activity of NOS in general or eNOS specifically.

A test for determining that eNOS activity is reduced is by assaying a reduction in wildtype Ras nitrosylation. This is carried out, for example, by capturing nitrosylated protein in blood by a biotin switch assay (Jaffrey, S. R., et al., Nat. Cell. Biol. 3, 193-197 (2001)), followed by immunoblot in the commercially available Ras antibodies as outlined in Lim, K.-H., et al, Nature, Vol. 452, No. 3, pp 646-650 and Supplementary Information therefor, 3 Apr. 2008.

One agent useful for this purpose is L-NAME, i.e. $N^G$-nitro-L-arginine methyl ester (dosage ranging from 0.5 to 4 mg/kg body weight). L-NAME is commercially available. Another agent and dosages thereof useful for this purpose is L-NMMA, i.e $N^G$-monomethyl-L-arginine. (Dosage ranging from 0.1 to 0.2 mg/kg body weight). LMMA is commercially available.

We turn to inhibitors of expression of HRas, i.e., which prevent or reduce expression of wildtype HRas.

One agent useful for this purpose is a published siRNA (Yang, G., et al., Oncogene 22, 5694-5701 (2003)) identified in the Sequence Listing as SEQ ID NO: 3; that efficiently knocks down the expression of HRas proteins and, as shown by the applicant, inhibits tumor growth in cells and in mice and is considered to do the same in humans. The siRNA of SEQ ID NO: 3 is produced as follows: Complementary oligonucleotides obtained from Integrated DNA Technologies (Coralville, USA) and annealed together were cloned into the Hind III and Bgl II sites of pSUPER-RETRO (OligoEngine, Seattle, Wash.). The sense strand of this insert is identified in the Sequence Listing as SEQ ID NO: 6. Transcription of this sequence by RNA polymerase produces an shRNA having the sequence identified in the Sequense Listing as SEQ ID NO: 7. This is processed using Dicer complex to remove the hairpin to give the double stranded RNA sequence of SEQ ID NO: 3 which specifically knocks down the expression of human HRas.

A test for determining that HRas expression is reduced is by immunoblot by using commercially available HRas antibody.

Dosage for this agent is, for example is 100-1600 micrograms based on a clinical trial of the siRNA compound AGN211745.

We turn to inhibitors of expression of NRas, i.e., which prevent or reduce expression of wildtype NRas.

One agent useful for this purpose is a novel siRNA generated by the applicant identified in the Sequence Listing as SEQ ID NO: 2; that efficiently knocks down the expression of NRas proteins and inhibits tumor growth in cells and in mice and is considered to do the same in humans. The siRNA of SEQ ID NO: 2 is produced as follows: Complementary oligonucleotides obtained from Integrated DNA Technologies (Coralville, USA) and annealed together were cloned into the Hind III and Bgl II sites of pSUPER-RETRO (OligoEngine, Seattle, Wash.). The sense strand of this insert is identified in the Sequence Listing as SEQ ID NO: 8. Transcription of this sequence by RNA polymerase produces an shRNA having the sequence identified in the Sequense Listing as SEQ ID NO: 9. This is processed using Dicer complex to remove the hairpin to give the double stranded RNA sequence of SEQ ID NO: 2 which specifically knocks down the expression of human NRas.

A test for determining that NRas expression is reduced is by immunoblot by using commercially available NRas antibody.

Dosage for this agent is, for example, is 100-1600 micrograms based on a clinical trial of the RNAi compound AGN211745.

We turn to inhibitors of the activity of HRas and NRas. These include farnysl transference inhibitors, e.g. R115777 (tipifarnib) and SCH66336 (e.g. oral dosage for R157777 ranging from 50 mg/kg to 100 mg/kg; e.g. oral dosage for SCH66336 ranging from 250-350 mg/day).

We turn now to inhibitors of activation of wildtype Ras by activated eNOS, that is which prevent nitrosylation of wildtype Ras proteins at C118.

These can be determined by testing compounds for causing loss of wildtype Ras nitrosylation. This is carried out, for example, by capturing nitrosylated protein in blood by a biotin switch assay (Jaffrey, S. R., et al., Nat. Cell. Biol. 3, 193-197 (2001)), followed by immunoblot in the commercially available Ras antibodies as outlined in Lim, K.-H., et al, Nature, Vol. 452, No. 3, pp 646-650 and Supplemental Informative therefore, 3 Apr. 2008.

Suitable inhibitors of Ras nitrosylation include antioxidants including ascorbic acid, α-tocopherol and polyphenols, e.g. resveratrol, catochin, caffeic acid, flavone, cinnanic acid, avbotin.

Determination of dosage for these types of inhibitors is by measuring loss of Ras nitrosylation in blood by capturing nitrosylated proteins as described above followed by immunoblot with commercially available Ras antibody as described above.

Routes of administration of the inhibitors which are not siRNAs are oral and intravenous.

For administration of the siRNAs into humans, the human infected with the plasmid for producing the desired shRNA to produce an siRNA (Dicer complex is in cells, so the shRNA will be processed) or the human can be injected with oligonucleotides alone or encapsulated in lipid vesicles that encode the sequence corresponding to the desired siRNA.

The term "therapeutically effective amount" means tumor initiating inhibiting effective amount or tumor growth inhibiting effective amount or amount causing loss of wildtype Ras nitrosylation The invention is supported by the following Background Examples and illustrated by the following Working Example.

Background Example 1

Determination of Akt-eNOS-(Wildtype)Ras Pathway for Oncogenic Ras Drive Cancers

We have demonstrated that oncogenic Ras-driven tumor growth depends upon activation of Akt, a known target of Ras, through activation of eNOS through phosphorylation of S1177 of eNOS by activated Akt. Moreover, we have demonstrated that activated Akt activation of eNOS leads to S-nitrosylation at C118 and correspondingly activation of wildtype Ras proteins, and that this activation of wildtype Ras proteins is required for tumor growth. Specifically, we demonstrated that inhibition of Akt signaling reduces S1177 phosphorylation of eNOS, and that knockdown of eNOS in human cancer cells or knockout of eNOS in mice rescues Ras driven tumor growth. We have demonstrated that Ras driven tumor growth is rescued by expression of wildtype eNOS, but not S1177A mutant version, reinforcing the notion that it is indeed Akt-mediated activation needed for tumor growth of eNOS, not simply the expression of eNOS. Moving down the signaling pathway, we have further demonstrated that loss of eNOS expression reduces C118 S-nitrosylation of wildtype Ras proteins, and moreover, that knockdown of NRas or HRas inhibits the tumorigenic growth of oncogenic KRas-driven human cancer cell lines. Importantly, we have demonstrated this loss of tumor growth by knocking down either NRas or HRas is rescued by expressing wildtype NRas or HRas, but not a C118S mutant that cannot be S-nitrosylated. In summary, we have discovered that oncogenic Ras promotes tumor growth through Akt activation, leading to phosphorylation and activation of eNOS at S1177, and that activated eNOS in turn leads to the nitrosylation of wildtype Ras proteins at C118, leading to their activation and tumorigenic function.

Experiments that evidence these demonstrations in cells and mice are set forth in Lin, K.-H., Ancrile, B. B., Kashatus, D. F., and Counter, C. M., titled "Tumour maintenance is mediated by eNOS" Lim, K.-H., et al, Nature, Vol. 452, No. 3, pp 646-650 and Supplemental Informative therefor, 3 Apr. 2008, the whole of which is incorporated herein by reference.

Background Example 2

Immuno Compromised Mice Injected with Human Pancreatic Cancer Cells have Tumor Growth Inhibited by Feeding of L-NAME Methods for creating stably infected cell lines are set below:

Day 1
Morning—split a 10 cm plate of confluent 293T/17 cells (ATCC CRL-11268) 1:6 in αMEM supplemented with 10% Fetal Calf Serum (FCS) (no antibiotics) into a 10 cm plate so as to be 40-50% confluent at time of transfection.

Day 2
Morning—mix in tissue culture hood in microcentrifuge tube: 12 µg pCL-10A1, 3 µg pSUPER-RETRO-PURO plasmid (OligoEngine, Seattle, Wash.) engineered to encode eNOS, RNA, NRas siRNA or HRas siRNA, and serum free media to 200 µl total volume. Tap tube side gently to mix and incubate at room temperature 15-45 minutes. Add dropwise to 293T/17 cells with micropipette and incubate overnight at 37° C.

Day 3
Morning—repeat transfection protocol from day 2. Once the transfection mix is added to the cells, it must be incubated for at least 8 hours. Evening—remove media and replace with 6 ml of cell specific media of cells to be infected.

Day 4
Morning—split a confluent 10 cm plate of pancreatic cancer cell line to be infected in cell type specific media so that they will reach 25-35% confluency the following morning.

Day 5
Morning—aspirate media in a 10 ml syringe, attach 0.45 µm acrodisc filter to the bottom of the syringe. Filter the media into a 15 ml conical tube. To the media, add 5 µl polybrene (800 µg/ml. Mix gently by tapping the side of the tube with finger. Remove media from pancreatic cancer cells to be infected and replace with the filtered virus containing media. Add 2 ml of fresh cell type specific media to ensure enough growth factors.

Day 6
Morning—remove virus-containing media from pancreatic cancer cells and replace with fresh cell type specific media.

Day 8
Morning—place pancreatic cancer cells under selection utilizing the cell type specific media supplemented with the appropriate selection agent (puromycin). Amounts of common selecting agents and the duration of selection are carried out depending on the cell line; however, a kill curve should be done on specific cells to ensure proper selection.

Method of testing pancreatic cancer cell line for tumor growth is set forth below:
1. Expand pancreatic cancer cells stably infected with pSUPER-RETRO-PURO plasmid (OligoEngine) engineered to encode eNOS siRNA, NRas siRNA, or HRas siRNA to a total count of at least $1 \times 10^7$ cells/mouse, typically 4-8 15 cm tissue culture dishes at full confluency (number of dishes determined by cell size).
2. Trypsinize each plate utilizing 2 ml trypsin and resuspend each plate with 4 ml 1×PBS. Place each 6 ml suspension into one common 50 ml conical tube.
3. Spin down cells 3 minutes at 500×g.
4. Resuspend pellets and wash with 30 ml 1× phosphate buffered saline (PBS). Spin down cells as in step 3.
5. Aspirate off PBS and resuspend pellet in 3 ml 1×PBS/plate.
6. Count cells utilizing hemocytometer.
7. Add $1 \times 10^7$ cells/mouse to a 50 ml conical tube, spin down as in step 3.
8. Aspirate PBS and mix 100 µl matrigel/mouse with the cell pellet.
9. Draw the slurry into a sterile 1 mL syringe with attached 25 gauge needle. Inject equal parts subcutaneously (under the skin without injecting into the muscle or peritoneum) into the flanks of SCID-beige immunocompromised mice. (The Jackson Laboratory, Bar Harbor, Me.).
10. Weigh each mouse for baseline reading and track tumor progression over the weeks to months by measuring large and small diameters and extrapolating tumor volume utilizing the equation: Tumor Volume=(small diameter)$^2$+(large diameter/2).

Eight SCID-beige immunocompromised mice. (The Jackson Laboratory, Bar Harbor, Me.). were each injected simultaneously with one million cells of the human pancreatic cell line MiaPaCa-2 (available from the ATCC, identified as ATCC CRL-1420). Then 4 mice were provided with drinking water supplemented with L-NAME at a concentration of 0.5 g/liter and 4 were provided with drinking water that was not supplemented. Measurements were taken at the site of the injection to calculate tumor volume. Results are shown in FIG. 1 which is a graph of Tumor Volume vs. Time in days after injection where the diamonds denote measurements on untreated mice and the triangles denote measurements on L-NAME fed mice. Tumors grew more slowly and exhibited almost a 3-fold reduction in size (p<0.01) at the termination of the experiment when the mice were provided with drinking water supplemented with L-NAME were compared to mice that were provided with untreated drinking water. The experiment indicates that eNOS is a valid pharmacologic target that can be inhibited with available small molecule inhibitors for treatment of pancreatic cancer.

Working Example I

A forty year old male presents with symptoms of severe upper abdominal pain which is relieved by bending forward, weight loss, diabetes and symptoms of glucose intolerance.

Diagnosis of pancreatic cancer is made by MRI of the pancreas and pancreas-associated antigen CA19-9.

The patient is administered wortmannin intravenously to establish a blood level of 300 nm for two weeks. Pain is ameliorated and CA19-9 levels decrease.

Testing for wildtype Ras nitrosylation shows reduction compared to status before administration.

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A method for treating a human patient affected with oncogenic Ras-driven cancer comprising administering to said patient a therapeutically effective amount of $N^G$-nitro-L-arginine methyl ester (L-NAME).

2. The method of claim 1, wherein the cancer is selected from the group consisting of pancreatic cancer, non-small-cell lung adenocarcinoma, colorectal cancer, follicular thyroid cancer, undifferentiated papillary thyroid cancer, seminoma, melanoma, bladder cancer, liver cancer, kidney cancer, myelodysplastic syndrome and acute myelogenous leukemia.

3. The method of claim 2, wherein the cancer is pancreatic cancer.

4. The method of claim 1, wherein the L-NAME is administered at a dosage ranging from 0.5 to 4 mg/kg body weight.

5. The method of claim 1, wherein the L-NAME is administered orally or intravenously.

* * * * *

```
                          SEQUENCE LISTING

<160> NUMBER OF SEQ ID NOS: 9

<210> SEQ ID NO 1
<211> LENGTH: 21
<212> TYPE: RNA
<213> ORGANISM: Homo sapiens

<400> SEQUENCE: 1
aagaguuaua agauccgcuu c                                           21

<210> SEQ ID NO 2
<211> LENGTH: 21
<212> TYPE: RNA
<213> ORGANISM: Homo sapiens

<400> SEQUENCE: 2
caagaagagu acagugccau g                                           21

<210> SEQ ID NO 3
<211> LENGTH: 21
<212> TYPE: RNA
<213> ORGANISM: Homo sapiens

<400> SEQUENCE: 3
ggcaagagug cgcugaccau c                                           21

<210> SEQ ID NO 4
<211> LENGTH: 51
<212> TYPE: DNA
<213> ORGANISM: Homo sapiens

<400> SEQUENCE: 4
aagagttata agatccgctt cttcaagaga gaagcggatc ttataactct t          51

<210> SEQ ID NO 5
<211> LENGTH: 51
<212> TYPE: RNA
<213> ORGANISM: Homo sapiens

<400> SEQUENCE: 5
aagaguuaua agauccgcuu cuucaagaga gaagcggauc uuauaacucu u          51

<210> SEQ ID NO 6
<211> LENGTH: 51
<212> TYPE: DNA
<213> ORGANISM: Homo sapiens

<400> SEQUENCE: 6
ggcaagagtg cgctgaccat cttcaagaga gatggtcagc gcactcttgc c          51

<210> SEQ ID NO 7
<211> LENGTH: 51
<212> TYPE: RNA
<213> ORGANISM: Homo sapiens

<400> SEQUENCE: 7
```

```
ggcaagagug cgcugaccau cuucaagaga gauggucagc gcacucuugc c            51

<210> SEQ ID NO 8
<211> LENGTH: 51
<212> TYPE: DNA
<213> ORGANISM: Homo sapiens

<400> SEQUENCE: 8
caagaagagt acagtgccat gttcaagaga catggcactg tactcttctt g            51

<210> SEQ ID NO 9
<211> LENGTH: 51
<212> TYPE: RNA
<213> ORGANISM: Homo sapiens

<400> SEQUENCE: 9
caagaagagu acagugccau guucaagaga cauggcacug uacucuucuu g            51
```